United States Patent
Su et al.

(10) Patent No.: US 10,416,085 B2
(45) Date of Patent: Sep. 17, 2019

(54) DISTRIBUTED OPTICAL FIBER IDENTIFICATION SYSTEM AND METHOD FOR SEEPAGE CONDITIONS OF HYDRAULIC STRUCTURE AND BASE THEREOF

(71) Applicant: Hohai University, Nanjing, Jiangsu (CN)

(72) Inventors: Huaizhi Su, Jiangsu (CN); Meng Yang, Jiangsu (CN)

(73) Assignee: Hohai University, Nanjing, Jiangsu (CN)

( * ) Notice: Subject to any disclaimer, the term of this patent is extended or adjusted under 35 U.S.C. 154(b) by 160 days.

(21) Appl. No.: 15/736,484

(22) PCT Filed: Jan. 8, 2016

(86) PCT No.: PCT/CN2016/070442
§ 371 (c)(1),
(2) Date: Dec. 14, 2017

(87) PCT Pub. No.: WO2016/201967
PCT Pub. Date: Dec. 22, 2016

(65) Prior Publication Data
US 2018/0195969 A1    Jul. 12, 2018

(30) Foreign Application Priority Data

Jun. 19, 2015 (CN) .................. 2015 1 03451746

(51) Int. Cl.
*G01N 21/85* (2006.01)
*B23P 19/04* (2006.01)
(Continued)

(52) U.S. Cl.
CPC .............. *G01N 21/85* (2013.01); *B23P 19/04* (2013.01); *G01K 11/00* (2013.01); *G01K 11/32* (2013.01); *G01N 21/21* (2013.01); *G01N 21/88* (2013.01)

(58) Field of Classification Search
CPC ........ G01N 21/85; G01N 21/21; G01N 21/88; G01K 11/32; G01K 11/00; B23P 19/04
See application file for complete search history.

(56) References Cited

FOREIGN PATENT DOCUMENTS

| CN | 104977233 | 10/2015 |
|---|---|---|
| CN | 204789002 | 11/2015 |

(Continued)

OTHER PUBLICATIONS

Written Opinion and International Search Report for International patent application No. PCT/CN2016/070442, dated Mar. 28, 2016, 13 pages.

*Primary Examiner* — Hina F Ayub
(74) *Attorney, Agent, or Firm* — Rankin, Hill & Clark LLP

(57) ABSTRACT

A distributed optical fiber identification system and method for seepage conditions of a hydraulic structure and a base thereof including a single-mode optical fiber having an automatic control heat source produced for seepage measurement, an optical path coupler and a synchronous controller, the synchronous controller is connected to a mode locked laser, a polarization beam splitter, an isolator, a grating pair, a diffraction grating, a reflector, a beam splitter, a nonlinear crystal, a spectrometer and a Michelson interferometer, the output end of the Michelson interferometer is connected to the optical path coupler, the output end of the optical path coupler is connected to a detector and a second optical splitter respectively, the detector is connected to a digital signal processor, the second optical splitter is connected to the digital signal processor through an amplifying (Continued)

circuit, and the digital signal processor is connected to the synchronous controller and a collector respectively.

9 Claims, 2 Drawing Sheets

(51) Int. Cl.
*G01N 21/21* (2006.01)
*G01N 21/88* (2006.01)
*G01K 11/00* (2006.01)
*G01K 11/32* (2006.01)

(56) References Cited

FOREIGN PATENT DOCUMENTS

| | | |
|---|---|---|
| CN | 204789261 | 11/2015 |
| CN | 105181362 | 12/2015 |

DISTRIBUTED OPTICAL FIBER IDENTIFICATION SYSTEM AND METHOD FOR SEEPAGE CONDITIONS OF HYDRAULIC STRUCTURE AND BASE THEREOF

BACKGROUND

Seepage is an important factor in the safe and long-term service of a hydraulic structure, and particularly to earth-rock and particulate structures including earth-rock dams and embankments, and so on, the seepage problem and the influence thereof are increasingly serious. It is of very important significance to ensure the engineering safety to research and develop an advanced, practical and reliable wading structure seepage detection instrument, and strengthen the rational arrangement and the efficient transmission of monitoring data and the scientific processing analysis so as to accurately identify the seepage conditions of the structure. With the rapid development of optical fiber sensing technology and the continuous development of the application fields thereof, it has become an important research topic and application direction in the optical fiber sensing technology to use the optical fiber sensing technology to detect the internal temperature changes of the wading structure and utilize the correlative mechanism of the temperature and the seepage to indirectly achieve the monitoring and identification of the seepage conditions of the structure.

A. G. S. Smekal firstly predicted from theory that after the light entered a medium, scattered light with frequency changes would appear excluding reflection and refraction. Moreover, researches show that the interaction between a photon and a phonon is processed in the form of absorbing or emitting the phonon; if a scattering phenomenon occurs when the photon absorbs or emits the phonon, the scattering of absorbing or emitting an optical phonon is called Raman scattering, and the scattering of absorbing or emitting the acoustical phonon is called Brillouin scattering, and the scattering is weakest in back-scattering light. Frequency shift occurs in both Raman scattering and Brillouin scatterings, wherein the frequency shift of Brillouin scattering is caused by sound waves or phonon waves of an acoustic branch, while the frequency shift of Raman scattering is caused by the vibration in molecules or phonon waves of an optical branch. Since the phonon describes lattice vibration, and the acoustic branch describes the motion of atomic mass centre, the frequency shift volume of Raman scattering light is unrelated to the wavelength of the incident light, and only depends on the medium properties. Further, it is considered in a quantum theory that Raman scattering is caused by the inelastic collision between the photon and a medium molecule, and the inelastic collision further leads to the transfer of energy, i.e., being represented as jumping of the molecular energy level, or absorbing the phonon and converting to scattered light with a higher frequency, or emitting the phonon and converting to scattered light with a lower frequency. When the medium molecule in a ground state jumps to an excited state through the high energy level where the incident photon is located, it will produce a Stokes photon with a lower frequency, while the medium molecule in the excited state jumps to the ground state from the high energy level after absorbing the incident photon, it produces an anti-stokes photon with a higher frequency. When being applied in a huge amount, the intensity of the anti-stokes light and the Stokes light will be continuously increased. Researches to the Raman scattering light have found that only the light intensity of the anti-stokes light is sensitive to the temperature, while neither the wavelength of the Stokes light nor the wavelength of the Raman scattering light is affected by the temperature.

According to the basic theory above, a lot of temperature and seepage measurement systems based on Raman scattering light are developed currently, but the intensity of Raman scattering light is weak, and the signal after the photoelectric conversion will be covered by a variety of noises, the signal to noise ratio is very poor, however the signal to noise ratio is often one of the most important factors determining the temperature measurement precision of the system or the distance measurement of the system. The traditional methods of increasing the signal to noise ratio include: increasing the peak power of pump pulse light, while this method has the disadvantage that when the peak power of the pulse light exceeds the nonlinear threshold of the optical fiber, a nonlinear effect will occur to Raman scattering, while the nonlinear effect will seriously interfere with the temperature demodulation; and the second method is to conduct equalization processing on the collected data repeatedly, but an overlong monitoring distance will spend much time and consume huge memory for processing, which greatly reduces the real-time reaction capacity on temperature measurement. Therefore, the spatial resolution, the length of the sensing optical fiber, the uncertainty of the temperature measurement and the measurement time become the important factors to determine the performance of the distributed optical fiber Raman temperature sensor system.

At present, the most common distributed optical fiber temperature system (Distributed Optical Fiber Temperature System, DTS) measures the temperature on the basis of the property that the Raman back-scattering light is modulated by the temperature. Since the intensity of the Raman scattering light is very weak, the DTS system is essentially a technology to process and detect weak signals, which uses the anti-stokes Raman scattering light as a temperature measurement signal, uses the single laser pulse as a pump signal, and uses the Stokes and Raman scattering light as a reference channel for temperature measurement, but has the disadvantages that the pulse width is uneasy to adjust, the spatial resolution is low, and the signal to noise ratio is poor. With the development, there are some new technologies, and those with representativeness include a distributed optical fiber temperature sensor integrated with an optical fiber Raman amplifier, a distributed optical fiber Raman temperature sensor using pulse coding technology, a distributed optical fiber temperature sensor using a Raman-related dual wavelength self-tuning technology, and a distributed optical fiber temperature sensor embedded with an optical switch.

The distributed optical fiber temperature sensor integrated with an optical fiber Raman amplifier only amplifies and increases analog electronic signals, but does not solve the problems of pulse width and signal to noise ratio fundamentally. The distributed optical fiber Raman temperature sensor using a pulse coding technology mainly aims to a single-mode optical fiber, and needs to adopt complicated coding and decoding technologies in order to improve the signal to noise ratio as well as the signal extraction and resolving ability of the system, which greatly increases the operation difficulty and the design complexity of equipment, but still has large deficiencies from the aspects of the final spatial resolution and the signal to noise ratio of the system. For the distributed optical fiber temperature sensor using a Raman-related dual wavelength self-tuning technology, using dual light sources cannot preferably ensure the same loss of the temperature measurement optical fibers of the two channels in the same band yet, and the temperature demodulation curve of the distributed optical fiber temperature sensor will still have the problems of incline, distortion, etc. For the distributed optical fiber temperature sensor embedded with an optical switch, although the temperature measurement optical fiber can be expanded into multiple channels from one channel by increasing the optical switch, the precision and measurement timeliness thereof are very difficult to ensure.

On the other hand, most of the seepage monitoring technologies based on the sensing optical fiber at current need to use an external circuit to heat the optical fiber; therefore, the optical fiber is required to have a heating function, and a set of complete heating circuit needs to be built as well, which greatly increases the manufacture cost of the optical fiber. Moreover, since it is difficult to coordinate the relationship between the voltage of the external circuit and the heating optical fiber during indoor and outdoor monitoring, the heating optical fiber generated will often have the phenomenon of instable or excessive voltage in this case, and the condition of soft fiber jacket and even charred fiber jacket will be caused in a short period of time due to the difficulty to control the voltage, which causes extremely serious damage to the operator and the instrument. In addition, when it is applied to the on-site monitoring of actual engineering, necessary security measures are often deficient, and t a heating circuit is more difficult to lay; particularly to dam and other water conservancy and hydropower engineering, since most of the engineering are located in remote regions, the service environment is extremely serious, and the achievement of the layout of optical fiber and heating function is more difficult, and even failed.

Based on the background and the current condition above, it is urgently needed to conduct major revolution and research to the optical fiber seepage measurement technology from the hydraulic seepage monitoring characteristics and special working environment, so as to provide technical support to fundamentally solve the problems of spatial resolution, signal to noise ratio, heating, and truly achieve the hydraulic seepage optical fiber monitoring with super-high spatial resolution, super-long sensing distance, super-high temperature and seepage measurement precision and super-high measurement efficiency.

TECHNICAL FIELD

The present invention relates to a system and a method for monitoring seepage of a hydraulic structure and a base thereof, and more particularly, to a distributed optical fiber identification system for seepage conditions of a hydraulic structure and a base thereof and a monitoring method in a harsh environment.

Wherein: 100 refers to module configured with a remote cloud database, 101 refers to dam safety monitoring information management and analysis assessment system, 102 refers to synchronous controller, 103 refers to mode locked laser, 104 refers to first wavelength division multiplexer, 105 refers to polarization beam splitter, 106 refers to isolator, 107 refers to nonlinear amplifier, 108 refers to grating pair, 109 refers to liquid-crystal spatial light modulator, 110 refers to diffraction grating, 111 refers to reflector, 112 refers to beam splitter, 113 refers to nonlinear crystal, 114 refers to spectrograph, 115 refers to Michelson interferometer, 116 refers to optoelectronic switch, 117 refers to master femtosecond pulse, 118 refers to auxiliary femtosecond pulse, 119 refers to first amplifier, 120 refers to second amplifier, 121 refers to first optical splitter, 122 refers to first optical splitter, 123 refers to second optical filter, 124 refers to third optical filter, 125 refers to second wavelength division multiplexer, 126 refers to second optical filter, 127 refers to optical path coupler, 128 refers to detector, 129 refers to thermostatic chamber, 130 refers to seepage monitoring region, 131 refers to first photodiode, 132 refers to second photodiode, 133 refers to third photodiode, 134 refers to third amplifier, 135 refers to fourth amplifier, 136 refers to first amplifier, 137 refers to Reyleigh optical receiver, 138 refers to anti-Stokes receiver, 139 refers to Stokes receiver, 140 refers to digital signal processor, 141 refers to collector, 142 refers to computer, 143 refers to single-mode optical fiber having an automatic control heat source specifically produced for seepage measurement, 200 refers to third transition protrusion end, 201 refers to outer circular sheathing protection pipes, 202 refers to second transition protrusion end, 203 refers to first transition protrusion end, 204 refers to gauze through-hole of first filter screen, 205 refers to first filter screen, 206 refers to second filter screen, 207 refers to gauze through-hole of second filter screen, 208 refers to drainage water storage cotton sleeve, 208 refers to heat insulation steel ring, 210 refers to inner protective elastic layer, 211 refers to single-core optical fiber, 212 refers to inner-layer filling protection ring, 213 refers to elastic hard ring, and 214 refers to anti-seepage heat insulation hard sleeve ring.

DETAILED DESCRIPTION

The present invention is further explained with reference to the drawings hereinafter.

Figure 1:
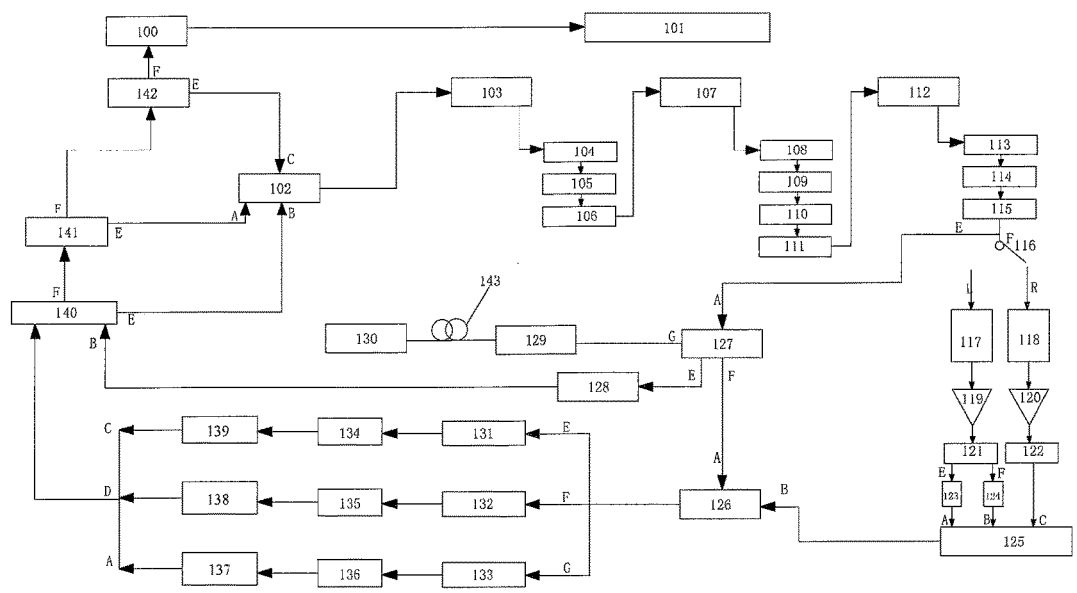
FIG. 1 is a structural diagram of a system of the present invention.
Figure 2:
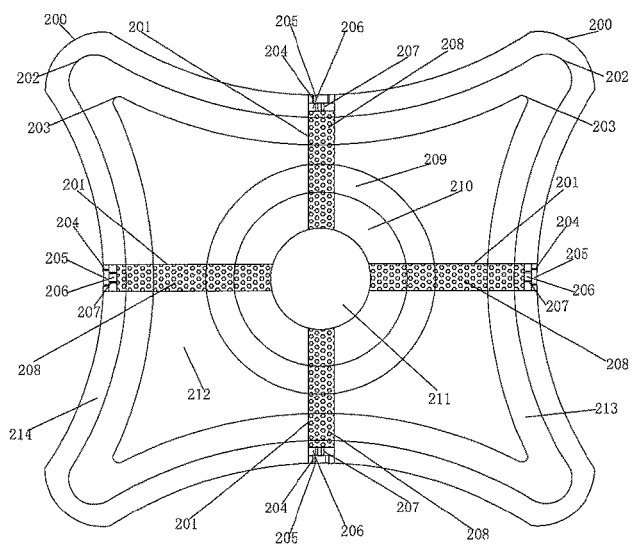
FIG. 2 is a structural schematic diagram of a single-mode optical fiber having an automatic control heat source specifically produced for seepage measurement in FIG. 1.
Figure 3:
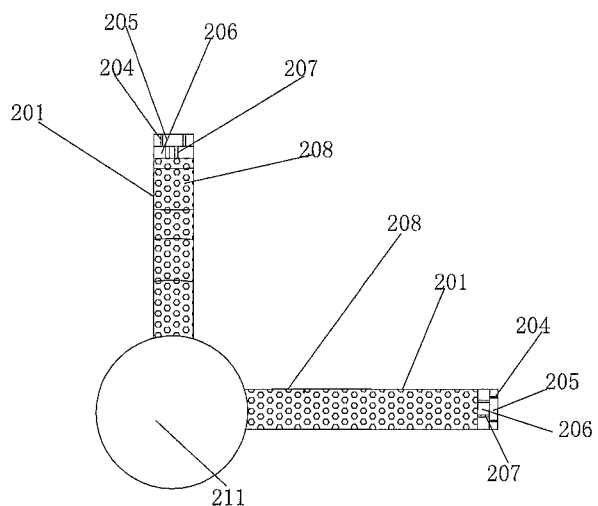
FIG. 3 is a detailed structural diagram of outer circular sheathing protection pipes in FIG. 2.

As shown in FIG. 1 to FIG. 3, the present invention provides, a distributed optical fiber identification system for seepage conditions of a hydraulic structure and a base thereof, comprising a single-mode optical fiber having an automatic control heat source specifically produced for seepage measurement 143 laid in a hydraulic structure seepage monitoring region 130 in a vertically staggered manner as well as an optical path coupler 127 and a synchronous controller 102 connected to the single-mode optical fiber having an automatic control heat source specifically produced for seepage measurement 143, wherein a monitoring thermostatic chamber 129 is arranged between the specifically produced single-mode optical fiber for automatic control heat source seepage measurement 143 and the optical path coupler 127, the synchronous controller 102 is connected to a mode locked laser 103, a first wavelength division multiplexer 104, a polarization beam splitter 105, an isolator 106, a nonlinear amplifier 107, a grating pair 108, a liquid-crystal spatial light modulator 109, a diffraction grating 110, a reflector 111, a beam splitter 112, a nonlinear crystal 113, a spectrograph 114 and a Michelson interferometer 115 in sequence, the output end of the Michelson interferometer 115 is connected to the optical path coupler 127 and the optoelectronic switch 116 simultaneously, the output end of the optical path coupler 127 is respectively connected to a detector 128 and a second optical splitter 126, the detector 128 is connected to a digital signal processor 140, the second optical splitter 126 is connected to the digital signal processor 140 through an amplifying circuit, the amplifying circuit comprises a first amplifying circuit, a second amplifying circuit and a third amplifying circuit in parallel connection, the first amplifying circuit comprises a first photodiode 131, a third amplifier 134 and a Stokes receiver 139 connected in sequence, the second amplifying circuit comprises a second photodiode 132, a fourth amplifier 135 and an anti-Stokes receiver 138 connected in sequence, the third amplifying circuit comprises a third photodiode 133, a fifth amplifier 136 and a Reyleigh optical receiver 137 connected in sequence, and the first photodiode 131, the second photodiode 132 and the third photodiode 133 are respectively connected to the output end of the second optical splitter 126; the output end of the Michelson interferometer 115 is connected to an optoelectronic switch 116 simultaneously, the optoelectronic switch 116 is provided with an L-side switch and an R-side switch, the L-side switch is connected to the input end of a master femtosecond pulse 117, the R-side switch is connected to an auxiliary femtosecond pulse 118, the master femtosecond pulse light of the master femtosecond pulse 117 can enter the optical signal input end of the first amplifier 119, the auxiliary femtosecond pulse light of the auxiliary femtosecond pulse 118 can enter the optical signal input end of the second amplifier 120, the optical signal output port of the first amplifier 119 is connected to the input port of a first optical splitter 121, the output port of the first optical splitter 121 is respectively connected to the signal input port of a second optical filter 123 and the signal input port of a third optical filter 124, the optical signal output port of the second amplifier 120 is connected to the optical signal input end of a first optical filter 122, the output ends of the first optical filter 122, the second optical filter 123 and the third optical filter 124 are connected to the input end of a second wavelength division multiplexer 125, and the output end of the second wavelength division multiplexer 125 is connected to the input end of the second optical splitter 126; the output end of the digital signal processor 140 is respectively connected to the synchronous controller 102 and a collector 141, the output end of the collector 141 is respectively connected to the synchronous controller 102 and a computer 142, the computer 142 is connected to a module configured with a remote cloud database 100, and the module configured with a remote cloud database 100 collects and conveys information to a dam safety monitoring information management and analysis assessment system 101.

In the present invention, the single-mode optical fiber having an automatic control heat source specifically produced for seepage measurement 143 is provided with a single-core optical fiber 211, an inner protective elastic layer 210, a heat insulation steel ring 209, an inner-layer filling protection ring 212, an elastic hard ring 213, and an anti-seepage heat insulation hard sleeve ring 214 arranged in sequence from inside to outside. The single-core optical fiber 211 is respectively connected to a plurality of outer circular sheathing protection pipes 201, the outer circular sheathing protection pipes 201 sequentially pass through the inner protective elastic layer 210, the heat insulation steel ring 209, the inner-layer filling protection ring 212 and the elastic hard ring 213 in sequence and are connected to the anti-seepage heat insulation hard sleeve ring 214, each outer circular sheathing protection pipe 201 is filled with a drainage water storage cotton sleeve 208, the drainage water storage cotton sleeve 208 is connected to a second filter screen 206, the second filter screen 206 is provided with a gauze through-hole 207 of the second filter screen, the second filter screen 206 is connected to a first filter screen 205 externally, and the first filter screen 205 is provided with a gauze through-hole 204 of the first filter screen. The elastic hard ring 213 and the anti-seepage heat insulation hard sleeve ring 214 are irregular quadrilateral frames, the four sides of the quadrilateral frame are depressed inwards, and the four corners of the quadrilateral frame are round corners, which are respectively a third transition protrusion end 200, a second transition protrusion end 202, and a first transition protrusion end 203 formed by the anti-seepage heat insulation hard sleeve ring 214, the elastic hard ring 213 and the inner-layer filling protection ring 212. The aperture of the gauze through-hole 204 of the first filter screen 205 arranged on the first filter screen 205 is greater than the aperture of the gauze through-hole 207 of the second filter screen arranged on the second filter screen 206, and the difference of the aperture of the two gauze through-holes is more than two times. Both the first filter screen 205 and the second filter screen 206 are located inside the anti-seepage heat insulation hard sleeve ring 214.

In the present invention, the signal output port of the synchronous controller 102 is connected to the signal input port of the mode locked laser 103, and under the joint action of the synchronous controller 102 and the mode locked laser 103, an ultra-short pulse with a narrow pulse width and a high peak power is generated, an signal the mode shift laser generated by the mode locked laser 103 passes through the first wavelength division multiplexer 104 and reaches the polarization beam splitter 105, the combined use of the first wavelength division multiplexer 104 and the polarization beam splitter 105 enhances the pumping power and implements the combination of pumping sources, the optical signal passing through the polarization beam splitter 105 reaches the isolator 106, the input optical signal of the polarization beam splitter 105 is converted and outputted and finally collected to the optical signal input port of the nonlinear amplifier 107, the optical signal passing through the nonlinear amplifier 107 interacts with phonons, and an optical signal is amplified, then the optical signal output port of the nonlinear amplifier 107 is connected to the optical signal input port of the grating pair 108, the grating pair 108 conducts wave vector modulation on the optical signal and is connected to the liquid-crystal spatial light modulator 109 thereafter, so as to acquire a laser signal with more gains and narrower pulse width; the optical signal output port of the liquid-crystal spatial light modulator 109 is connected to the optical signal input end of the diffraction grating 110, optical dispersion occurs to the light beam passing through the diffraction grating 110, then the dispersed optical signal passes through the reflector 111 and is switched onto the beam splitter 112, the optical signal output end of the beam splitter 112 focuses the femtosecond pulse to form optical spectrums through the nonlinear crystal 113, the reflector 111, the beam splitter 112 and nonlinear crystal 113 and the nonlinear crystal 113, and then the optical spectrums pass through the optical signal input end of the spectrograph 114, the optical signal output end of the spectrograph 114 is connected to the optical signal input end of the Michelson interferometer 115, an optical wave passing through the spectrograph 114 is calibrated and the length and refractive index of the optical wave are measured, the optical signal output port E of the Michelson interferometer 115 is connected to an input end interface A of the optical path coupler 127, the optical signal output port F of the Michelson interferometer 115 is connected to the optoelectronic switch 116, the optoelectronic switch 116 is provided with an L-side switch and an R-side switch, the L-side switch is connected to the input end of the master femtosecond pulse 117, and the R-side switch is connected to the auxiliary femtosecond pulse 118.

In the present invention, the femtosecond pulse is separated, amplified and filtered so as to introduce the femtosecond pulse into a distributed optical fiber temperature measurement and demodulating system, wherein the process is as follows: the master femtosecond pulse light of the master femtosecond pulse 117 will enter the optical signal input end of the first amplifier 119, the auxiliary femtosecond pulse light of the auxiliary femtosecond pulse 118 will pass through the optical signal input end of the second amplifier 120, the optical signal output port of the first amplifier 119 is connected to the input port of the first optical splitter 121, the output port F of the first optical splitter 121 is connected to the signal input port of the third optical filter 124, the optical signal output port of the second amplifier 120 is connected to the signal input port of the first optical filter 122, the input end A of the second wavelength division multiplexer 125 is connected to the output end of the second optical filter 123, the input end B of the second wavelength division multiplexer 125 is connected to the output end of the third optical filter 124, the input end C of the second wavelength division multiplexer 125 is connected to the output end of the first optical filter 122, and the input end D of the second wavelength division multiplexer 125 is connected to the end B of the second optical splitter 126; in order to transmit three optical signals carrying different information on one optical fiber simultaneously, the second wavelength division multiplexer 125 and the second optical splitter 126 are used herein, wherein the output end F of the optical path coupler 127 is connected to the input end A of the second optical splitter 126 to separate the optical fiber signals reflecting external changes through the second optical splitter 126; the output end E of the second optical splitter 126 is connected to the input end of the first photodiode 131, the output end F of the second optical splitter 126 is connected to the input end of the second photodiode 132, the output end G of the second optical splitter 126 is connected to the input end of the third photodiode 133, the output port of the first photodiode 131 is connected to the signal input end of the third amplifier 134, the output port of the second photodiode 132 is connected to the signal input end of the fourth amplifier 135, the output end of the third photodiode 133 is connected to the signal input end of the fifth amplifier 136, the output end of the fifth amplifier 136 is connected to the signal input end of the Reyleigh optical receiver 137, the output end of the fourth amplifier 135 is connected to the input end of the anti-Stokes receiver 138, the output end of the third amplifier 134 is connected to the input end of the Stokes receiver 139, the input end of the anti-Stokes receiver 138, the input end of the Stokes receiver 139 and the input end of the Reyleigh optical receiver 137 are connected to the input end of the ports A, D and C of the digital signal processor 140, the optical signals carrying external loads or changes caused by temperature changes are separated into three optical paths carrying three kinds of optical information via the second optical splitter 126, and are collected by the photodiode, the amplifier and receiver respectively corresponding to the three optical paths; the output end E of the optical path coupler 127 is connected to the input end of the detector 128, the detector 128 converts the femtosecond pulse optical signal on the single-mode optical fiber having an automatic control heat source specifically produced for seepage measurement 143 into an electrical signal to conduct detection, calibration and collection, the output end of the detector 128 is connected to the port B of the digital signal processor 140, the output port E of the digital signal processor 140 is connected to the input port B of the synchronous controller 102, the output port F of the digital signal processor 140 is connected to the input end of the collector 141, the output port E of the collector 141 is connected to the input port A of the synchronous controller 102, the output port F of the collector 141 is connected to the signal input end of the computer 142, the signal output port E of the computer 142 is connected to the signal input end C of the synchronous controller 102, and the signal output port F of the computer 142 is connected to the signal input end of the module configured with a remote cloud database 100 to convey the collected information to the dam safety monitoring information management and analysis assessment system 101.

In the present invention, the information acquisition port G of the optical path coupler 127 is connected to the thermostatic chamber 129 via a section of single-mode optical fiber having an automatic control heat source specifically produced for seepage measurement 143, and the temperature acquired through the monitoring thermostatic chamber 129 is used as the temperature value for calibration, and the single-mode optical fiber having an automatic control heat source specifically produced for seepage measurement 143 after passing through the thermostatic chamber 129 is laid in the structure seepage monitoring region 130 in a vertically staggered manner.

A monitoring method of the above-mentioned distributed optical fiber identification system for seepage conditions of a hydraulic structure and a base thereof comprises the following steps.

In step 1, the single-core optical fiber 211 is pressed in the heat insulation steel ring 209, the inner protective elastic layer 210, the inner-layer filling protection ring 212, the elastic hard ring 213 and the anti-seepage heat insulation hard sleeve ring 214, and the outer circular sheathing protection pipes 201, the first filter screen 205, the second filter screen 206, the gauze through-hole 207 of the second filter screen and the gauze through-hole 204 of the first filter screen 205 to assemble a device component having functions of drainage, flow control, heat conduction and heat control; the structure is compacted and packaged according to a principle of constantly increasing the strength of materials from inside to outside, and the structure in the outermost layer shall have a strength higher than that of other layers, and shall also meet the requirements of corrosion protection, seepage prevention and thermal insulation, or the like.

In step 2, after the single-mode optical fiber having an automatic control heat source specifically produced for seepage measurement 143 is completely assembled, the synchronous controller 102 and the computer 142 are opened to conduct access verification on the single-mode optical fiber having an automatic control heat source specifically produced for seepage measurement 143 to be laid, then the single-mode optical fiber having an automatic control heat source specifically produced for seepage measurement 143 is horizontally and vertically laid in a structure region to be measured, so as to form grid optical fiber distribution in the space to be measured, the synchronous controller 102 and the computer 142 are opened to conduct secondary access detection on the laid single-mode optical fiber having an automatic control heat source specifically produced for seepage measurement 143, and the single-mode optical fiber having an automatic control heat source specifically produced for seepage measurement 143 is connected to the optical path coupler 127 through the thermostatic chamber to 129 complete the assembling of the entire system, wherein multiple single-mode optical fibers having an automatic control heat source specifically produced for seepage measurement 143 need to be laid in parallel in a complicated structure region for standby service.

In step 3, switches to be measured in the distributed optical fiber identification system for seepage conditions of a hydraulic structure and a base thereof are turned on to debug the system, the special optical fiber for seepage measurement single-mode optical fiber having an automatic control heat source specifically produced for seepage measurement 143 is connected to conduct calibration graduation, each channel is tested, the pulse light information of the single-mode optical fiber having an automatic control heat source specifically produced for seepage measurement 143 is modulated through the synchronous controller 102 after there are no mistakes, the pulse light information data is collected through the collector 141, and then the data information is collected into the computer 142 for feedback analysis, so as to adjust and control the synchronous controller 102, the finally collected information is collected into the dam security monitoring information management and analysis assessment system 101 through the module configured with a remote cloud database 100.

In step 4, when the seepage water passes through a hydraulic structure region to be measured, double layer diameter-variable filtering is conducted on particle impurity in the seepage water by means of the gauze through-hole 204 of the first filter screen 205 on the first filter screen 205 and the gauze through-hole 207 of the second filter screen on the second filter screen 206, and the seepage water is continuously and directly contacted with the single-core optical fiber 211 from four directions through the storage, filtering and drainage functions of the drainage water storage cotton sleeve 208, thus forming actual temperature difference.

In step 5, the temperature difference field of the measured structure caused by the temperature difference on the horizontal and vertical single-mode optical fibers having an automatic control heat source specifically produced for seepage measurement 143 is drawn; in a region that the seepage water flows, the seepage water will exchange heat with a hydraulic structure and a base thereof to be measured, then partial heat will be taken away by the seepage water, and a local part of the temperature difference field will be suddenly changed, while this part is namely the location where seepage occurs; further, when the seepage water forms a channel for a free surface of water in the hydraulic structure to be measured, the relative caloric value taken away by the exchange between the water body and the outside is substantially equal at every place of the channel at a certain moment; therefore, the places with the same temperature difference values are connected along the upstream and downstream structure faces of the hydraulic structure, and intersection lines among the places with the same temperature difference values and the upstream and downstream structure faces of the hydraulic structure are namely seepage lines.

In step 6, the collected spatio-temporal data of the single-mode optical fiber having an automatic control heat source specifically produced for seepage measurement is collected to the module configured with a remote cloud database 100 through the computer 142, and the information is collected into the module of the dam safety monitoring information management and analysis assessment system 101, so as to dynamically monitor and identify the seepage states of the hydraulic structure and the base thereof.

Those described above are merely preferred embodiments of the invention It should be noted that, those having ordinary skills in the art can make a plurality of improvements and modifications without departing from the principle of the invention, and those improvements and modifications all fall in the scope of protection of the invention.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A distributed optical fiber identification system for seepage conditions of a hydraulic structure and a base thereof, comprising: a single-mode optical fiber having an automatic control heat source specifically produced for seepage measurement laid in a hydraulic structure and a base seepage monitoring region thereof in a vertically staggered manner as well as an optical path coupler and a synchronous controller connected to the single-mode optical fiber having an automatic control heat source specifically produced for seepage measurement, wherein a monitoring thermostatic chamber is arranged between the specifically produced single-mode optical fiber for automatic control heat source seepage measurement and the optical path coupler, the synchronous controller is connected to a mode locked laser, a first wavelength division multiplexer, a polarization beam splitter, an isolator, a nonlinear amplifier, a grating pair, a liquid-crystal spatial light modulator, a diffraction grating, a reflector, a beam splitter, a nonlinear crystal, a spectrograph and a Michelson interferometer in sequence, the output end of the Michelson interferometer is connected to the optical path coupler, the output end of the optical path coupler is respectively connected to a detector and a second optical splitter, the detector is connected to a digital signal processor, the second optical splitter is connected to the digital signal processor through an amplifying circuit, the output end of the digital signal is respectively connected to the synchronous controller and a collector, the output end of the collector is respectively connected to the synchronous controller and a computer, the computer is connected to a module configured with a remote cloud database, and the module configured with a remote cloud database collects and conveys information to a dam safety monitoring information management and analysis assessment system.

2. The distributed optical fiber identification system for seepage conditions of a hydraulic structure and a base thereof according to claim 1, wherein the amplifying circuit comprises a first amplifying circuit, a second amplifying circuit and a third amplifying circuit in parallel connection, the first amplifying circuit comprises a first photodiode, a third amplifier and a Stokes receiver connected in sequence, the second amplifying circuit comprises a second photodiode, a fourth amplifier and an anti-Stokes receiver connected in sequence, the third amplifying circuit comprises a third photodiode, a fifth amplifier and a Reyleigh optical receiver connected in sequence, the first photodiode, the second photodiode and the third photodiode are respectively connected to the output end of the second optical splitter.

3. The distributed optical fiber identification system for seepage conditions of a hydraulic structure and a base thereof according to claim 2, wherein the output end of the Michelson interferometer is connected to an optoelectronic switch simultaneously, the optoelectronic switch is provided with an L-side switch and an R-side switch, the L-side switch is connected to the input end of a master femtosecond pulse, the R-side switch is connected to an auxiliary femtosecond pulse, the master femtosecond pulse light of the master femtosecond pulse can enter the optical signal input end of the first amplifier, the auxiliary femtosecond pulse light of the auxiliary femtosecond pulse can enter the optical signal input end of the second amplifier, the optical signal output port of the first amplifier is connected to the input port of a first optical splitter, the output port of the first optical splitter is respectively connected to the signal input port of a second optical filter and the signal input port of a third optical filter, the optical signal output port of the second amplifier is connected to the optical signal input end of a first optical filter, the output ends of the first optical filter, the second optical filter and the third optical filter are connected to the input end of a second wavelength division multiplexer, and the output end of the second wavelength division multiplexer is connected to the input end of the second optical splitter.

4. The distributed optical fiber identification system for seepage conditions of a hydraulic structure and a base thereof according to claim 3, wherein the single-mode optical fiber having an automatic control heat source specifically produced for seepage measurement is provided with a single-core optical fiber, an inner protective elastic layer, a heat insulation steel ring, an inner-layer filling protection ring, an elastic hard ring, and an anti-seepage heat insulation hard sleeve ring arranged in sequence from inside to outside, wherein the single-core optical fiber is connected to a plurality of outer circular sheathing protection pipes separately, the outer circular sheathing protection pipes sequentially pass through the inner protective elastic layer, the heat insulation steel ring, the inner-layer filling protection ring and the elastic hard ring in sequence and are connected to the anti-seepage heat insulation hard sleeve ring, each outer circular sheathing protection pipe is filled with a drainage water storage cotton sleeve, the drainage water storage cotton sleeve is connected to a second filter screen, the second filter screen is provided with a gauze through-hole of the second filter screen, the second filter screen is connected to a first filter screen externally, and the first filter screen is provided with a gauze through-hole of the first filter screen.

5. The distributed optical fiber identification system for seepage conditions of a hydraulic structure and a base thereof according to claim 4, wherein the elastic hard ring and the anti-seepage heat insulation hard sleeve ring are irregular quadrilateral frames, the four sides of the quadrilateral frame are depressed inwards, and the four corners of the quadrilateral frame are round corners.

6. The distributed optical fiber identification system for seepage conditions of a hydraulic structure and a base thereof to claim 5, wherein the aperture of the gauze through-hole of the first filter screen arranged on the first filter screen is greater than the aperture of the gauze through-hole of the second filter screen arranged on the second filter screen, and the difference of the aperture of the two gauze through-holes is more than two times.

7. The distributed optical fiber identification system for seepage conditions of a hydraulic structure and a base thereof according to claim 6, wherein four outer circular sheathing protection pipes are arranged, and respectively located on 0-degree, 90-degree, 180-degree and 270-degree radix directions of the single-core optical fiber.

8. The distributed optical fiber identification system for seepage conditions of a hydraulic structure and a base thereof according to claim 7, wherein both the first filter screen and the second filter screen are located inside the anti-seepage heat insulation hard sleeve ring.

9. A sensing method of the distributed optical fiber identification system for seepage conditions of a hydraulic structure and a base thereof, comprising the following steps of:

step 1: pressing the single-core optical fiber in the heat insulation steel ring, the inner protective elastic layer, the inner-layer filling protection ring, the elastic hard ring and the anti-seepage heat insulation hard sleeve ring, and using the outer circular sheathing protection pipes, the first filter screen, the second filter screen, the gauze through-hole of the second filter screen and the gauze through-hole of the first filter screen to assemble a device component having functions of drainage, flow control, heat conduction and heat control;

step 2: after the single-mode optical fiber having an automatic control heat source specifically produced for seepage measurement is completely assembled, opening the synchronous controller and the computer to conduct access verification on the single-mode optical fiber having an automatic control heat source specifically produced for seepage measurement, then horizontally and vertically laying the single-mode optical fiber having an automatic control heat source specifically produced for seepage measurement in a structure region to be measured, so as to form grid optical fiber configuration in the space to be measured, opening the synchronous controller and the computer to conduct secondary access detection on the laid single-mode optical fiber having an automatic control heat source specifically produced for seepage measurement, and connecting the single-mode optical fiber having an automatic control heat source specifically produced for seepage measurement to the optical path coupler through the thermostatic chamber to complete the assembling of the entire system, wherein multiple single-mode optical fibers having an automatic control heat source specifically produced for seepage measurement need to be laid in parallel in a complicated structure region for standby service;

step 3: turning on switches to be measured in the distributed optical fiber identification system for seepage conditions of a hydraulic structure and a base thereof to debug the system, connecting the special optical fiber for seepage measurement single-mode optical fiber having an automatic control heat source specifically produced for seepage measurement to conduct calibration graduation, testing each channel, modulating the pulse light information of the single-mode optical fiber having an automatic control heat source specifically produced for seepage measurement through the synchronous controller after there are no mistakes, collecting the pulse light information data through the collector, and then collecting the data information into the computer for feedback analysis, so as to adjust and control the synchronous controller, collecting and conveying the finally collected information into the dam safety monitoring information management and analysis assessment system through the module configured with a remote cloud database;

step 4: when the seepage water passes through a hydraulic structure region to be measured, conducting double layer diameter-variable filtering on particle impurity in the seepage water by means of the gauze through-hole of the first filter screen on the first filter screen and the gauze through-hole of the second filter screen on the second filter screen, and continuously and directly contacting the seepage water with the single-core optical fiber from four directions through the storage, filtering and drainage functions of the drainage water storage cotton sleeve, thus forming actual temperature difference; and step 5: drawing the temperature difference field of the hydraulic structure and the base thereof measured by the horizontal and vertical single-mode optical fibers having an automatic control heat source specifically produced for seepage measurement.

* * * * *